(12) United States Patent
Ganey

(10) Patent No.: US 9,179,954 B2
(45) Date of Patent: *Nov. 10, 2015

(54) BONE SCREW FASTENER

(71) Applicant: Vivex Biomedical Inc., Marietta, GA (US)

(72) Inventor: Timothy Ganey, Tampa, FL (US)

(73) Assignee: Vivex Biomedical, Inc., Marietta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/594,850

(22) Filed: Jan. 12, 2015

(65) Prior Publication Data

US 2015/0127057 A1    May 7, 2015

Related U.S. Application Data

(60) Continuation-in-part of application No. 13/737,043, filed on Jan. 9, 2013, now Pat. No. 9,015,922, which is a division of application No. 13/303,944, filed on Nov. 23, 2011, now Pat. No. 8,414,654.

(51) Int. Cl.
*A61B 17/86* (2006.01)
*A61B 17/70* (2006.01)
*A61F 2/30* (2006.01)
(Continued)

(52) U.S. Cl.
CPC ......... *A61B 17/8625* (2013.01); *A61B 17/7098* (2013.01); *A61B 17/866* (2013.01); *A61F 2/28* (2013.01); *A61F 2/30767* (2013.01); *A61C 8/0012* (2013.01); *A61F 2002/2835* (2013.01); *Y10T 29/49* (2015.01); *Y10T 29/49746* (2015.01)

(58) Field of Classification Search
CPC .............. A61C 8/0012; A61B 17/8625; A61F 2/30767
See application file for complete search history.

(56) References Cited

U.S. PATENT DOCUMENTS

| 3,852,045 A | 12/1974 | Wheeler et al. |
| 5,112,354 A | 5/1992 | Sires |
| 5,282,861 A | 2/1994 | Kaplan |

(Continued)

FOREIGN PATENT DOCUMENTS

| EP | 2338530 | 6/2011 |
| WO | 9939757 | 8/1999 |

(Continued)

OTHER PUBLICATIONS

St. John T.A., et al., Physical and Monetary Costs Associated With Autogenous Bone Graft Harvesting, Am. Journal of Orthopedics; 32:18-23, 2003.

(Continued)

*Primary Examiner* — Andrew Yang
(74) *Attorney, Agent, or Firm* — David L. King

(57) ABSTRACT

An improved bone screw for humans or mammals is a bone screw having exposed surfaces along a shank and threads extending from the shank with one or more selected portions of the exposed surfaces having a 3-dimensional pattern. The pattern provides enhanced resistance to thread loosening when affixed to bone. The exposed surface is on exterior portions of the threads or portions of the shank or both. The one or more selected portions of the exposed portions having a bone formation enhancing 3-dimensional patterns are in the external exposed thread surfaces or in the exposed shank surfaces or both.

21 Claims, 4 Drawing Sheets

(51) Int. Cl.
A61F 2/28 (2006.01)
A61C 8/00 (2006.01)

(56) References Cited

U.S. PATENT DOCUMENTS

| | | | |
|---|---|---|---|
| 6,419,491 | B1 | 7/2002 | Ricci |
| 7,018,418 | B2 | 3/2006 | Amrich et al. |
| 7,901,462 | B2 | 3/2011 | Yang et al. |
| 2003/0059742 | A1 | 3/2003 | Webster et al. |
| 2003/0125739 | A1 | 7/2003 | Bagga et al. |
| 2008/0221688 | A1* | 9/2008 | Trieu et al. .............. 623/17.16 |
| 2010/0036502 | A1 | 2/2010 | Svrluga |
| 2015/0157425 | A1* | 6/2015 | Bar Shalom .............. 433/174 |

FOREIGN PATENT DOCUMENTS

| | | |
|---|---|---|
| WO | 2006044832 | 4/2006 |
| WO | 2008115160 | 9/2008 |

OTHER PUBLICATIONS

Olson G.B., Computational Design of Hierarchically Structured Materials, Science; 277: 1237-1242, 1997.
Liao H., et al., Response of rat osteoblast-like cells to microstructured model surfaces in vitro, Biomaterials 24: 649-54, 2003.
Clover J. and Dodds R.A., Integrin subunit expression by human osteoblasts and osteoclasts in situ and in culture, J. Cell Sci; 103: 267-271, 1994.
Ingber D.E., Cellular Tensegrity: Exploring How Mechanical Changes in the Cytoskeleton Regulate Cell Growth, Migration, and Tissue Pattern during Morphogenesis, Int. Rev. Cytol.; 150: 173-224, 1994.
Meazzini MC et al., Osteoblast Cytoskeletal Modulation in Response to Mechanical Strain In Vitro, J. Orthop. Res.;16: 170-180, 1998.
Ingber D.E., Tensegrity: The Architectural Basis of Cellular Mechanotransduction, Annu. Rev. Physiol.; 59: 575-599, 1997.
Bindermann I., et al., The Transduction of Mechanical Force into Biochemical Events in Bone Cells May Involve Activation of Phospholipase A2, Calcif Tissue Int.; 42: 261-266, 1988.
Somjen D., et al., Bone Remodeling Induced by Physical Stress Is Prostaglandin E2 Mediated, Biocim. Biophys. Acta; 627: 91-100, 1980.
Kurtz, Steven M; Devine, John N; PEEK biomaterials in trauma, orthopedic and spinal implants, Aug. 7, 2007, Biomaterials, 28, 4845-4869.
Nikolovski J., et al., FASEB J.; 17: 455-7, 2003.
Rozengurt E., et al., Cyclic AMP: A mitogenic signal for Swiss 3T3 cells, J. Cell Biol.; 78: 4392-4396, 1981.
Shen V., et al., Prostaglandins Change Cell Shape and Increase Intercellular Gap Junctions in Osteoblasts Cultured From Rat Fetal Calvaria, J. Bone Miner Res.; 1: 2443-249, 1986.
Chen C.S., et al., Geometric Control of Cell Life and Death, Science; 276: 1425-1428, 1997; Edmondson A.C., Bosten, 1987.
Jee W.S.S., et al., Effects of spaceflight on trabecular bone in rats, Am. J. Physiol.; 244: R310-R314, 1983.
Zerath E., et al., Effects of spaceflight on bone mineralization in the rhesus monkey, J. Appl. Physiol.; 81: 194-200, 1996.
Backup P.K., et al., Spaceflight results in reduced mRNA levels for tissue-specific proteins in the musculoskeletal system, Am. J. Physiol.; 266: E567-E573, 1994.
Holick MF, Perspective on the Impact of Weightlessness on Calcium and Bone Metabolism, Bone; 22: 105S-111S, 1998.
Caillot-Augusseas A., Lafage-Proust MH et al., Bone formation and resorption biological markers in cosmonauts during and after a 180-day spaceflight (Euromir 95), Clin. Chem.; 44: 578-585, 1998.
Sampath T.K. and Reddi A.H., Distribution of bone inductive proteins in mineralized and demineralized extracellular matrix, Biochem Biophys. Res. Commun.; 119: 949-54, 1984.
Ganey T.M., et al., Trabecular Parameters in Whale: Examining Naive Trabecular Conformation; 44th Annual Meeting, New Orleans, Louisiana, Orthopaedic Research Society, Mar. 16-19, 1998.
Wealthall, Rosamund J; Brooker, Lesley R; Macey, David J; Griffin, Brendan J. Fine structure of the mineralized teeth of the chiton Acanthopleura echinata (Mollusca: Polyplacophora). Journal of Morphology. 265(2): 165-175, 2005.
Harris S.A., et al., Effects of Orbital Spaceflight on Human Osteoblast Cell Physiology and Gene Expression, Bone 20(4) 26: 325-31, 2000.
Reddi A.H. and Huggins C.B., Proc. Soc. Exp. Biol. Med.; 143: 634-637, 1973.
Sampath T.K. and Reddi A.H., Importance of Geometry of the Extracellular Matrix in Endochondral Bone Differentiation, J. Cell. Biol.; 98: 2192-2197, 1984.
Borden M., et al., Structural and human cellular assessment of a novel microsphere-based tissue engineered scaffold for bone repair, Biomaterials; 24: 597-609, 2003.
Koob T.J., et al., Biocompatibility of NDGA-polymerized collagen fibers I. Evaluation of cytotoxicity with tendon fibroblasts in vitro, J. Biomed. Mat. Res.; 56: 31-39, 2001.
Koob T.J. and Hernandez D.J., Material properties of polymerized NDGA-collagen composite fibers: development of biologically based tendon constructs, Biomaterials; 23: 203-212, 2002.
Suzuki F. Roles of cartilage matrix proteins, chondromodulin-I and-II, in endochondral bone formation: a review. Connect Tissue Res. 1996;35(1-4):303-7.
Gamradt SC, Lieberman Jr. Genetic modification of stem cells to enhance bone repair. Ann Biomed Eng. Jan. 2004;32(1):136-47.
Sammarco VJ, Chang L. Modern issues in bone graft substitutes and advances in bone tissue technology. Foot Ankle Clin. Mar. 2002;7(1):19-41.
Department of Health and Human Services, Jul. 2, 2002; http://www.fda.gov/cdrh/mda/does/p000058.pdf.
Sikavitsas V.I., et al., Formation of three-dimensional cell/polymer constructs for bone tissue engineering in a spinner flask and a rotating wall vessel bioreactor, J. Biomed. Mat. Res.; 62: 136-146, 2002.
Jaiswal N., et al., Osteogenic Differentiation of Purified, Culture-Expanded Human Mesenchymal Stem Cells In Vitro, J. Cell Biochem.; 64: 295-312, 1997.
West D.C., et al., A Simplified in Situ Solubilization Procedure for the Determination of DNA and Cell Number in Tissue Cultured Mammalian Cells. Anal. Biochem.; 147: 289-295, 1985.
Koob T.J., et al., Biocompatibility of NDGA-polymerized collagen fibers II. Attachment, proliferation, and migration of tendon fibroblasts in vitro, J. Biomed. Mat. Res.; 56: 40-48, 2001.
Tavakoli M., et al; The use of power beams in surface modification, Medical Device Technology, vol. 18 No. 1, Jan.-Feb. 2007: TWI Ltd, 2007.
Elias Carlos Nelson, Titanium dental implant surfaces, Materia (Rio J.) vol. 15 No. 2 Rio de Janeiro 2010, online version ISSN 1517-7076.
Alekhin A.P., et al; Structural properties of the titanium dioxide thin films grown by atomic layer deposition at various numbers of reaction cycles, Applied Surface Science 257 (2010) 186-191.
Ogden, John A, Skeletal Injury in the Child, Third Edition, Springer, pp. 5-6.
Yeh, Chih-Ko and Rodan, Gideon A, Tensile Forces Enhance Prostaglandin E Synthesis in Osteoblastic Cells Grown on Collagen Ribbons, Dept of Oral Biology, University of Connecticut Health Center, Calcified Tissue International (1984) 36: S67-S71.

* cited by examiner

BONE SCREW FASTENER

RELATED APPLICATIONS

This application is a continuation in part of co-pending U.S. application Ser. No. 13/737,043 filed Jan. 9, 2013 entitled, "Bone Implants And Method Of Manufacture" which is a division of U.S. Pat. No. 8,414,654 filed on Nov. 23, 2011 entitled, "Bone Implants And Method Of Manufacture".

TECHNICAL FIELD

The present invention relates to an improved bone screw having an externally prepared surface characteristic to prevent loosening while simultaneously encouraging new bone growth.

BACKGROUND OF THE INVENTION

Bone screws are provided in a variety of shapes and sizes. The most common employ titanium or stainless steel as a preferred material for implantation. These screws are ideal in that they do not oxidize and are very compatible with the bone structure. These screws typically employ one or more helical threads. Many are self-tapping at the proximal tip or end. The distal end of the screw has a head or some physical construction to allow torquing the screw into the bone. The shank extends between the head and the tip end and is machined with the desired threads to engage the bone structure.

The bone structure has an interior of a softer more open trabecular spacing. This region. This region is somewhat spongy or elastic in nature. The outer region of the bone is hard and more densely formed cortical bone. This hard bone can provide an excellent region to cut threads into as the screw is tightened. Historically, the screws, once fully inserted, are used to anchor bone plates, spinal fusion spacers and rods commonly used in spinal surgical repairs and to hold bone fracture fragments together.

The very nature of the helix angle cut into the shank to form the threads creates a spiral ramp inclined slightly. The bone screws are made with the threads being sharp and highly polished to make the bone entry easier. This contributes to a phenomenon that induces the bone screw to loosen over time. Ideally, new bone ingrowth occurs to help hold the fastener in place, but the occurrence of screw loosening is such that many, if not most, bone screws use anti-back out or locking features to keep the bone screw held in the bone in the event the screw tends to loosen. Secondarily, when the screw loosens it can also lower the pull out forces required to tear through the threads in the bone.

These and other issues can be reduced by a recent discovery that was initially created to enhance bone ingrowth on the exterior surfaces of implants. It was discovered that polymers like those used in implantation and metals like titanium and stainless steel could have greatly enhanced bone formation by surface patterning.

In U.S. Pat. Nos. 8,535,388 B2; 8,414,654 B2 and U.S. Pat. No. 8,679,189 B1*, a unique surface pattern was disclosed what in a preferred embodiment mimics under-modelled marine mammal bone. This pattern has proven beneficial in plastic and metal implants including PEEK, stainless steel and titanium. Its continuous network of voids creates regions of enhanced osteoinductivity to enhance rapid new bone growth as explained in U.S. Pat. No. 8,414,654 B2. In practice, the creation of these patterns can be accomplished employing laser technology. This manufacturing ability allows the machining to occur on difficult to reach surfaces and angles. The inventor, when applying this capacity to implants made in the form of bone screws, has found remarkable added benefits which are described hereinafter.

SUMMARY OF THE INVENTION

An improved bone screw for humans or mammals is a bone screw having exposed surfaces along a shank and threads extending from the shank with one or more selected portions of the exposed surfaces having a 3-dimensional pattern. The pattern provides enhanced resistance to thread loosening when affixed to bone. The exposed surface is on exterior portions of the threads or portions of the shank or both. The one or more selected portions of the exposed portions having a bone formation enhancing 3-dimensional patterns are in the external exposed thread surfaces or in the exposed shank surfaces or both.

The 3-dimensional pattern can be a substantially continuous network having voids. The voids have a width in the range of about 30-1000 microns. At least 10 percent of said voids have a dimension of at least 30 microns. The voids have a depth into the selected surface of about 150 microns or less. The voids preferably have a medium width of 500-800 microns to mimic the open marrow regions of bone, so the screw when formed has a trabecular bone structure appearance.

Preferably, the bone screw is made of a metal suitable for implanting in a human or mammal. The metal is titanium or a titanium alloy or the metal can be stainless steel or a stainless steel alloy.

In one embodiment, the bone screw may include the 3-dimensional pattern to secure the screw to the skeletal bone structure with the pattern being on a proximal surface of the threads. The bone formation 3-dimensional pattern has a void to solid ratio mimicking a pre-natal cancellous bone in a human. The pattern mimics a marine or sea mammal bone structure. The sea or marine mammal is a whale or a dolphin. In that embodiment, the bone pattern exhibits the following characteristics

| BIOPSY | BV/TV | BS/BV | TbTh | TbSp | TbN | Ost # |
|---|---|---|---|---|---|---|
| Cross | 17.71 | 14.98 | 135.16 | 631.70 | 1.33 | 230/mm$^2$ |
| Long | 24.54 | 8.67 | 231.05 | 710.98 | 1.06 | 150/mm$^2$ |

The bone screw implant, at select portions, exhibits a stress neutral isotropic structure for enhancing bone formation. In another embodiment, the 3-dimensional pattern mimics denticles of shark skin. The 3-dimensional pattern has a faceting along the threads that is directionally low in resistance during screw installation and tightening and once installed and tightened against bone has increased loosening resistance. The faceting is preferably asymmetrical in relation to torque resistance. The 3-dimensional pattern has a surface texture that forms a surface topography that is repeated on a regular, irregular, isotropic or asymmetrical, orthogonal or random basis. The 3-dimensional pattern can be formed into a continuous network of troughs or channels. Alternatively, the 3-dimensional pattern can be formed into a continuous network of ridges or protrusions. The 3-dimensional pattern can be a combination of a continuous network of troughs or channels and ridges or protrusions.

It is believed important that the 3-dimensional pattern is positioned on at least that portion of the screw that engages the cortical bone on some of the exposed surfaces, if not the whole of the screw threads and shank.

BRIEF DESCRIPTION OF THE DRAWINGS

The invention will be described by way of example and with reference to the accompanying drawings in which.

DETAILED DESCRIPTION OF THE INVENTION

Figure 1:
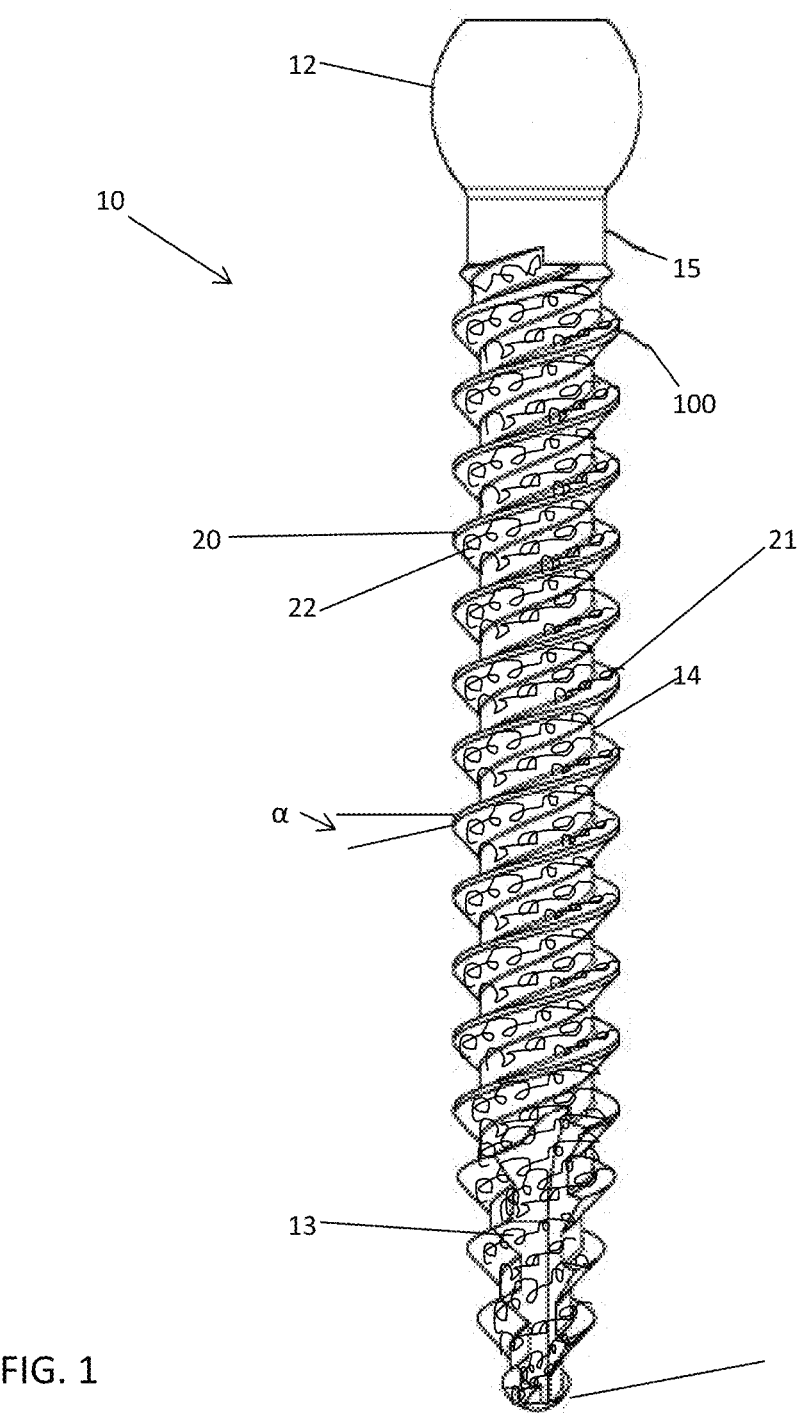
FIG. 1 is an exemplary bone screw made in accordance with the present invention.

With reference to FIG. 1, an exemplary bone screw 10 made in accordance with the present invention is illustrated. As shown, the bone screw 10 has a proximal tip end 11. As shown, the proximal tip end 11 has bone cutting flutes 13 to facilitate insertion of the bone screw 10 into a skeletal bone structure. As illustrated, the bone screw 10 has a shank 14. Radially extending outwardly from the shank 14 is a thread 20, the thread 20 can be one or more threads spirally wound about the shank 14 wherein the proximal surface 22 is on the underside of the thread 20 as shown and the distal surface 21 of the thread 20 is on an outer or upper surface of the thread 20 as it spirals about the shank 14. At the opposite end of the screw 10 is shown a screw head 12. In the illustrated embodiment, this screw head 12 has a shoulder 15 that allows the screw head 12 which has a somewhat spherical configuration to operate in a polyaxial fashion when mounted to a conventionally known tulip, not illustrated. The bone screw 10, as shown, has a pattern 100 extending along the shank 14 and along both sides 21, 22 of the threads in the illustrated embodiment.

Figure 2A:
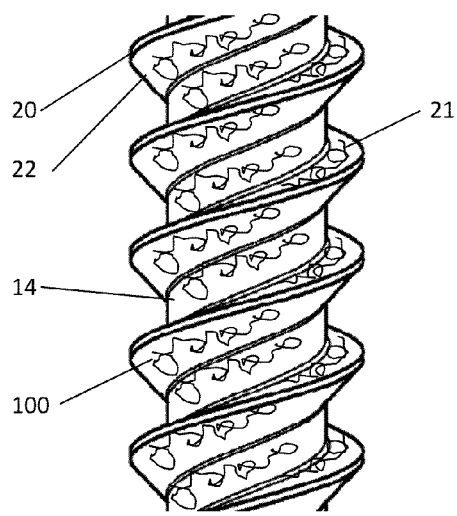
FIG. 2A is an enlarged portion of the bone screw of FIG. 1 showing an exemplary 3-dimensional pattern on the shank and the threads.
Figure 2B:
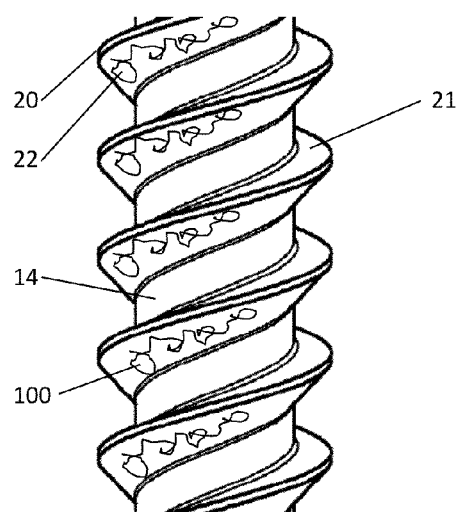
FIG. 2B is an enlarged portion of the bone screw showing the 3-dimensional pattern on the proximal side of the threads.

In FIG. 2A an alternative embodiment is shown wherein a portion of the thread 20 showing the exemplary 3-dimensional pattern 100 on the shank 14 and threads 20. The enlarged portion helps illustrate the patterning effect. In an alternative embodiment shown in FIG. 2B, the 3-dimensional pattern 100 is provided on proximal side 22 of the threads 20 or that side that first enters into the bone. Alternatively, no dimensional patterning is on the distal side 21 of the threads 20 or on the shank 14.

Figure 2C:
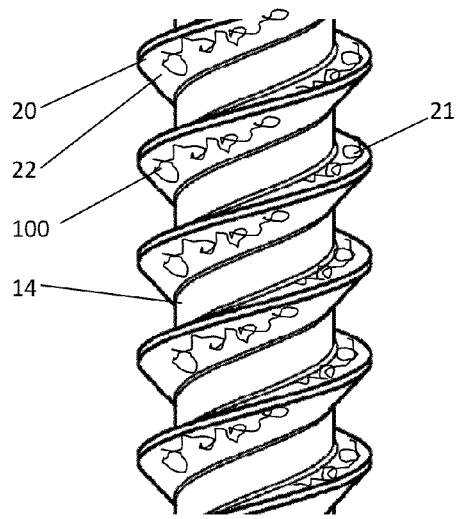
FIG. 2C is an enlarged portion of the bone screw showing the 3-dimensional pattern on the distal and proximal exposed thread surfaces.

In FIG. 2C, both sides of the threads 20 have a 3-dimensional pattern 100 on the distal and proximal exposed surfaces 21, 22 respectively while the shank 14 exhibits no pattern 100.

Figure 3A:
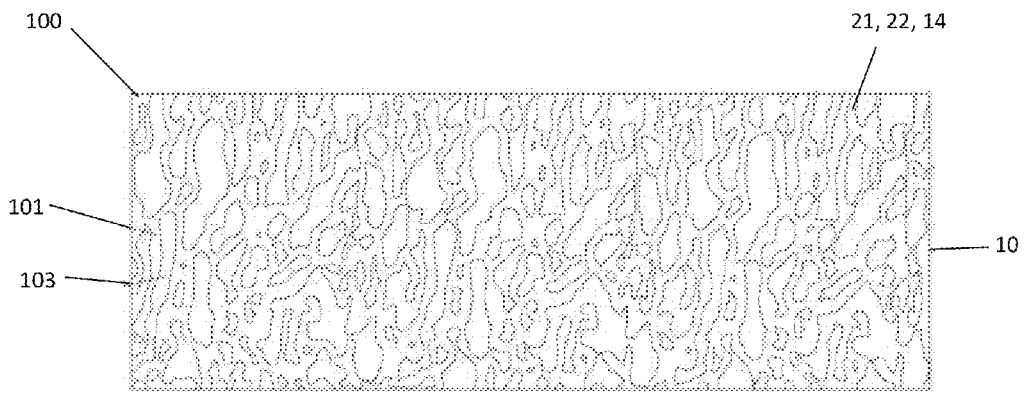
FIG. 3A is an enlarged plan view of a 3-dimensional first embodiment pattern having voids formed as troughs or channels.
Figure 3B:
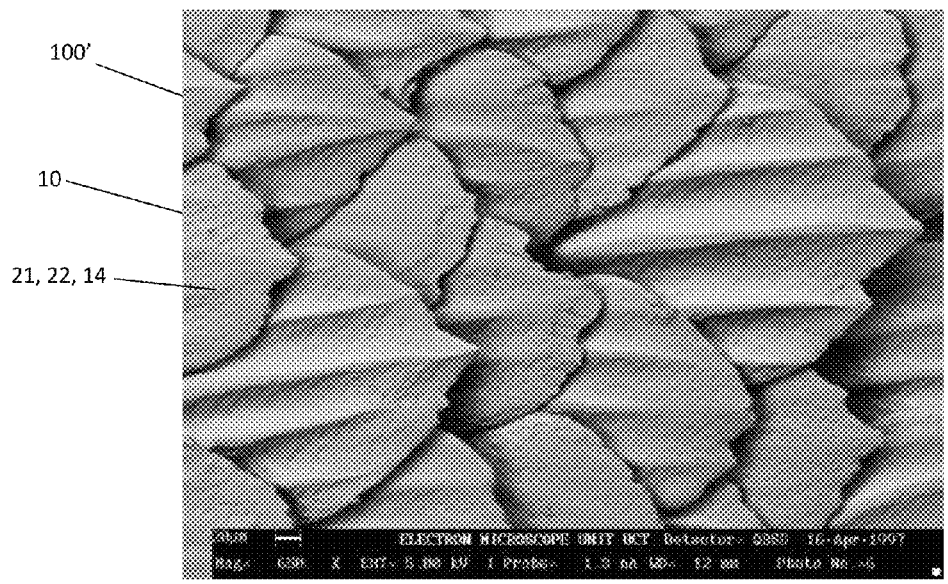
FIG. 3B is an alternative 3-dimensional pattern exhibiting ridges or protrusions.

It is believed that these patterns 100 when put on a metal, titanium or stainless steel, bone screw 10, will help enhance bone growth and new bone formation about the screw 10. These patterns 100 are very shallow in depth ranging from 50 to 150 µm and are prepared to create a continuous network of either ridges and protrusions or voids and troughs depending on the pattern selected. These patterns 100 ideally can mimic certain creatures found in nature. One pattern that is illustrated in FIG. 3A is a mimetic pattern that mimics an under- modelled trabecular bone structure of a marine mammal. In another embodiment, 3B, the pattern 100' is produced as a series of ridges or denticles mimicking the skin of a shark.

Figure 3C:
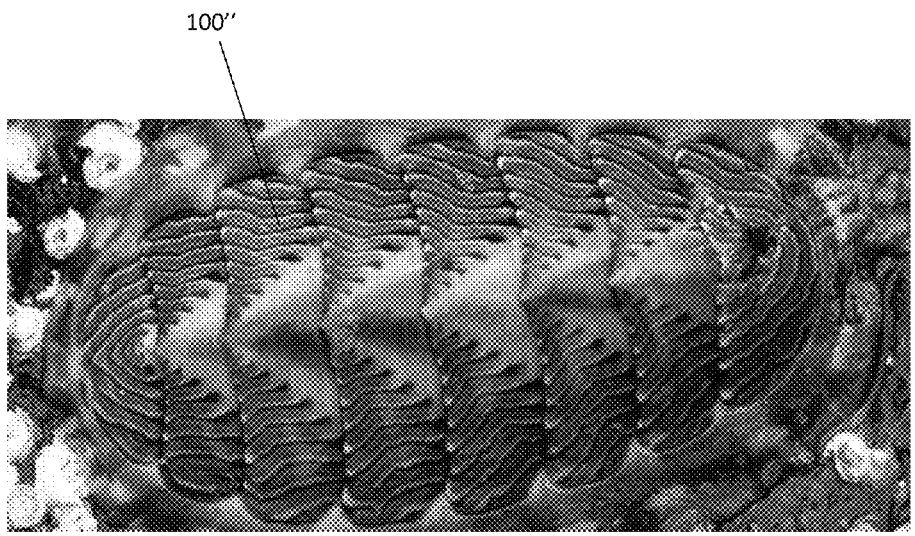
FIG. 3C is an alternative 3-dimensional pattern.

Several examples exist of form-driven biomineralization and mineral accretion. Given intention to secure screws in situ and to best affect a tight apposition, modeling the mimetics of shape driving invigorating the matrix-driven response seems a direct potential. In example, the major lateral teeth of the chiton Acanthopleura echinata, shown in FIG. 3C, are composite structures composed of three distinct mineral zones: a posterior layer of magnetite; a thin band of lepidocrocite just anterior to this; and apatite throughout the core and anterior regions of the cusp. Biomineralization in these teeth is a matrix-mediated process, in which the minerals are deposited around fibers, with the different biominerals occupying architecturally discrete compartments. The arrangement of the organic and biomineral components of the tooth is similar throughout the three zones, having no discrete borders between them, and with crystallites of each mineral phase extending into the adjacent mineral zone. Along the posterior surface of the tooth, the organic fibers are arranged in a series of fine parallel lines, but just within the periphery their appearance takes on a fish scale-like pattern, reflective of the cross section of a series of units that are overlaid, and offset from each other, in adjacent rows. The units are approximately 2 millimeter wide and 0.6 millimeter thick and comprise biomineral plates separated by organic fibers. Two types of subunits make up each 'fish scale': one is elongate and curved and forms a trough, in which the other, rod-like unit, is nestled. Adjacent rod and trough units are aligned into large sheets that define the fracture plane of the tooth. The alignment of the plates of rod-trough units is complex and exhibits extreme spatial variation within the tooth cusp. Close to the posterior surface the plates are essentially horizontal and lie in a lateromedial plane, while anteriorly they are almost vertical and lie in the posteroanterior plane. An understanding of the fine structure of the mineralized teeth of chitons, and of the relationship between the organic and mineral components, provides a new insight into biomineralization mechanisms and controls." As reported in Wealthall, Rosamund J; Brooker, Lesley R; Macey, David J; Griffin, Brendan J. Fine structure of the mineralized teeth of the chiton Acanthopleura echinata (Mollusca: Polyplacophora). Journal of Morphology. 265(2): 165-175, 2005.

In any event, when these patterns 100 are applied onto the exposed thread surfaces, they create areas onto which the bone can attach and attempt to enter to create new bone growth. Prior to that however, when a bone screw is tightened, it is very common over a period of time for the bone and threads 20 to loosen. It has been found that by providing these bone growth enhancing features on the screw threads 20, the screw threads 20 create a resistance to rotational movement that is quiet unexpected. Even the troughs and channel or ridges and protrusions created are substantially shallower than one would expect to facilitate in creating an anti-back out feature. However, it has been found if one looks at the thread helix angle α that spirals about a thread, you will see that it tends to ramp the thread surfaces in such a way that they would tend to loosen over time with any movement of the thread 20 or loads upon the screw itself. However, by providing a textured surface as is proposed in this invention, it has been determined that this loosening effect does not initiate. It is believed this is the equivalent of having a thread and bolt arrangement where the threads that engage the nut are rusty creating an oxidized surface that tends to prevent the threads from easily being dislodged. In the present case, since the bone screws 10 are made of titanium or stainless steel, oxidation does not easily occur next to the bone nor would one want it to. However, by providing a simulated network of mimetic patterns 100 on the threads 20 or the shank 14, it has been determined that this creates a tendency at the threads 20 to stay in position and not to release their tension on the cortical bone into which the screw 10 has been inserted.

It must be appreciated that the entry of bone screws 10 passes through a thin region of cortical bone that is very hard and readily accepts the threads being formed and enters in to a softer spongy region called the inner trabecular region. It is in this inner region where the threads have less ability to hold and grip into the spongy bone structure that are often known to pull out should the threads in the cortical bone region be damaged by over tightening or some other effect. By providing the network pattern 100 of the claimed invention, it has been determined that a physician can insert these screws and have a confidence level that they will not easily dislodge during normal use. While the invention facilitates the retention of the screw, it is understood that one may alternatively want to provide a separate anti-back out feature as is commonly done in the art. However, with the use of these patterns 100, it may be possible in some cases to eliminate any additional anti-back out mechanisms currently used in bone screws.

To better illustrate the pattern 100 used, each bone screw 10 is shown with the 3-dimensional pattern 100 illustrated as a magnified portion separate in a magnified rectangular region with a reference line pointing to the exposed surface. It is understood this pattern 100 is very small and, in order to visualize its appearance, this magnified surface region depicting the pattern 100 is provided. To try and illustrate the pattern 100 at true scale would result in the appearance of sandpaper of a fine grit similar to the skin of a shark. For this reason, the pattern 100 is shown separate and magnified, when in practice, the bone screw 10 actually can have the entire exposed surface covered by the pattern 100 or at least those portions near the cortical bone engagement. The 3-dimensional pattern 100 is made of a substantially continuous network having voids or indentations. The voids or indentations have a width of about 30-1000 microns. The voids have a depth into the selected surface of about 150 microns or less. In a preferred embodiment the 3-dimensional pattern mimics a marine or sea mammal bone structure such as a whale or dolphin. The voids preferably have a medium width of 500-800 microns mimicking the open marrow regions of bone so the 3-dimensional pattern on the bone screw, when formed, appears as a trabecular bone structure.

Alternatively, the improved bone screw 10 can be a machined or otherwise manufactured bone screw having a specific body structure 12 with exposed surfaces onto which the repeatable geometric 3-dimensional pattern 100 can be placed on selected portions of the exposed surface to create a continuous network of voids which will enhance bone formation, as shown in FIG. 1. With reference to FIG. 3A, the bone screw 10 has been magnified in size, such that the 3-dimensional pattern 100 is of a scale allowing for a better view of how the pattern is applied to the exposed surfaces. Exposed surfaces can be defined and developed throughout the screw 10 based on manufacturing technique, for example, the pattern can extend throughout the body structure of the screw using lasering or laser cutting.

It is most beneficial if the repeatable 3-dimensional geometric pattern 100 can be achieved as part of the initial manufacture of the bone screw 10. It must be appreciated that the size of the voids between the ridges 103 and channels 101 of the pattern 100 shown in FIG. 3A are extremely small and, as a result, such pattern formation to be repeatable in the surfaces can be assured by a secondary procedure of embossing, etching, micropatterning or pressing onto an exposed surface of the bone screw 10. Chemical etching, while feasible, can be used with the understanding the screw 10 must be free if any residual chemical that could be adverse to bone formation. Plasma deposition can also be used to form the pattern on the exposed surfaces of the device. Plasma-enhanced chemical vapor deposition (PECVD) is a process used to deposit thin films from a gas state (vapor) to a solid state on a substrate.

Most importantly, in the preferred embodiment, the geometric 3-dimensional pattern 100 is selected to duplicate or at least closely mimic the pattern of a marine mammal such as a whale. While this pattern 100 is preferred, other similar patterns that approach the void percentage depth and shape of a human pre-natal cellular structure are also considered optimal alternatives. The main distinction of this surface pattern 100 is that it is repeatable. Conventional surface treatments that roughen a surface to improve chemical adhesion simply do not achieve this ability to enhance bone formation about a bone screw. Whereas this repeatable pattern 100 has demonstrated this ability. Ideally, the bone screw 10, once prepared with a suitable 3-dimensional pattern 100, can be used in the surgical procedure for which it was designed without any alteration in the procedure with confidence that the prepared pattern surfaces 100 will facilitate new bone formation. Alternatively, more preferably, these improved bone screws 10 can be also treated with gels or coatings or sheets laden with bone formation enhancing cells which will find the patterned surfaces ideal for growth and adherence. Alternatively, the geometric 3-dimensional pattern 100 is selected to duplicate or at least closely mimic the pattern of a marine mammal such as a dolphin.

Once the geometric 3-dimensional pattern 100 is achieved in a reproducible manner on a selected surface of a bone screw 10, it can be coated or otherwise treated with cells to enhance bone creation and bone formation in the selected areas of the pattern or alternatively, the bone screw 10 can be simply implanted relying on the patient's tissue to attach and initiate bone formation de nova.

It is important to appreciate the improved device provides a beneficial surface to facilitate bone creation more quickly than in the absence of the 3-dimensional patterns. Furthermore, unlike a surface texture or roughening to enhance chemical bonding, the selected geometric patterns mimic pre-natal cancellous bone formation, which ideally, stimulates a biological response not otherwise appreciated or achieved in synthetic or metallic structures. The most common implants are load bearing devices with direction forces imparted due to the molding process. Isotropic structures are not bound in design by a vector of directional force. A biomaterial with no loading history supports integration that is singularly directed and substantially more efficient because it comes from a neutral state of loading, the forces guiding the new bone are biologically consistent with not the history of the material construction, but the combined geometry of the implant plus the regenerative potential of the construct. In instance, the intention of using the whale bone as a foundation material is that it has the same mechanical properties regardless of the direction of loading. This isotropy is a fundamental value to an inert prosthesis as it does not shield in any way the active loading signals during the fusion, or regenerative process. The integration is through the unit, not around the unit.

Typically the channels 101 having exposed surfaces with the pattern 100 of the bone screws 10 can optionally be filled with bone graft material either in a paste form or in solid bone material. This material during the patient's healing is expected to fuse with the adjacent vertebrae and by providing an envelope or covering so that the bone screw 10 will be more quickly fused to the spinal skeletal structure in a faster more rapid fashion due to the ability of the cells to trigger the regenerative process and to allow the adjacent bone structure to grow around the bone screw more quickly than would occur otherwise in the absence of the material.

Table 2 is the morphometric data of human cancellous bone samples H-1-H4 and whale cancellous bone W1. Briefly the entire specimen was imaged and the whale bone was purposely cut large to look for the internal consistency of the form to follow variation in scales of sizing. The cancellous bone samples range from 1-4 also in order of being most osteoporotic (1) and the number (4) specimen being the most normal bone. Number 3 specimen is likely an outlier and might sit adjacent to a cortical margin. The whale bone is consistent independent of boundary range or isometric randomization to size. The value in the whale bone is to isotropic distribution, thicker trabecula, greater trabecular spacing, and highest tissue density with lowest connectivity for equalized total volume. The importance is ridge dynamics, higher density with lesser void despite having greater separation makes this an ideal pattern for mimicking to enhance new bone growth in humans.

solid ratio of a pre-natal cancellous bone in a human or mammal and the pattern mimics a marine or sea mammal bone structure; and wherein the bone pattern exhibits the following characteristics;

| BIOPSY | BV/TV | BS/BV | TbTh | TbSp | TbN | Ost # |
|---|---|---|---|---|---|---|
| Cross | 17.71 | 14.98 | 135.16 | 631.70 | 1.33 | 230/mm² |
| Long | 24.54 | 8.67 | 231.05 | 710.98 | 1.06 | 150/mm². |

2. A bone screw for humans or mammals comprises:
a bone screw having exposed surfaces along a shank and threads extending from the shank;
one or more selected portions of the exposed surface having a 3-dimensional pattern, the pattern providing enhanced resistance to thread loosening when affixed to bone, wherein the exposed surface is on exterior portions of the threads or portions of the shank or both, wherein the one or more selected portions of the exposed portions having a bone formation enhancing 3-dimensional patterns are in the external exposed thread sur-

TABLE 2

| Sample No. | BVF (BV/TV) % | Trab. Thickness μm | Trab. Number 1/mm | Trab. Spacing μm | Connec. Density 1/mm³ | Apparent Density Mg/ccm HA | Tissue Density Mg/ccm HA | Total Volume mm³ | Bone Volume mm³ | SMI | Bone Surface mm² | BS/BV mm² | BS/TV 1/mm | BS/MV 1/mm | DA |
|---|---|---|---|---|---|---|---|---|---|---|---|---|---|---|---|
| | | | | | | Just within boundaries of pieces | | | | | | | | | |
| H1 | 14.6% | 142 | 1.41 | 653 | 6 | 65 | 888 | 570.999 | 83.594 | 1.7 | 1595.7 | 19.0 | 2.8 | 3.3 | 1.6 |
| H2 | 21.0% | 146 | 1.69 | 521 | 7 | 149 | 869 | 541.047 | 113.830 | 0.8 | 1989.8 | 17.2 | 3.7 | 4.7 | 2.8 |
| H3 | 24.0% | 191 | 1.65 | 525 | 6 | 185 | 917 | 417.510 | 100.217 | 1.0 | 1399.6 | 13.8 | 3.4 | 4.4 | 1.6 |
| H4 | 31.7% | 156 | 2.24 | 374 | 17 | 286 | 891 | 380.271 | 120.339 | 0.3 | 1908.7 | 15.6 | 5.0 | 7.3 | 1.7 |
| W1 | 21.1% | 183 | 1.20 | 800 | 3 | 190 | 866 | 1070.286 | 225.320 | 0.4 | 3126.6 | 13.7 | 2.9 | 3.7 | 1.4 |
| | | | | | | Smaller isometric cube ROI | | | | | | | | | |
| H1 | 15.9% | 139 | 1.63 | 578 | 6 | 87 | 890 | 70.113 | 11.152 | 1.9 | 208.8 | 18.9 | 3.0 | 3.5 | 1.6 |
| H2 | 24.0% | 150 | 1.80 | 488 | 8 | 186 | 871 | 70.113 | 16.798 | 0.8 | 277.5 | 16.4 | 4.0 | 5.2 | 2.4 |
| H3 | 26.3% | 174 | 1.78 | 487 | 8 | 218 | 911 | 70.113 | 18.451 | 0.9 | 266.0 | 14.4 | 3.8 | 5.1 | 1.7 |
| H4 | 34.6% | 156 | 2.36 | 360 | 18 | 319 | 882 | 70.113 | 24.256 | 0.0 | 372.6 | 15.2 | 5.3 | 8.1 | 1.7 |
| W1 | 21.1% | 167 | 1.29 | 768 | 3 | 226 | 897 | 70.113 | 14.780 | 0.3 | 212.9 | 14.3 | 3.0 | 3.8 | 1.5 |
| | | | | | | Smallest isometric cube ROI | | | | | | | | | |
| H1 | 16.5% | 144 | 1.63 | 577 | 5 | 94 | 892 | 45.084 | 7.457 | 1.8 | 134.3 | 18.1 | 3.0 | 3.6 | 1.6 |
| H2 | 24.9% | 152 | 1.88 | 471 | 8 | 194 | 870 | 45.084 | 11.219 | 0.8 | 180.5 | 16.1 | 4.0 | 5.3 | 2.3 |
| H3 | 26.6% | 173 | 1.82 | 475 | 7 | 221 | 908 | 45.084 | 11.993 | 0.9 | 172.6 | 14.4 | 3.8 | 5.2 | 1.8 |
| H4 | 35.3% | 155 | 2.41 | 352 | 19 | 326 | 880 | 45.084 | 15.903 | −0.1 | 243.7 | 15.2 | 5.4 | 8.4 | 1.7 |
| W1 | 20.4% | 166 | 1.32 | 754 | 3 | 220 | 902 | 45.084 | 9.178 | 0.4 | 134.6 | 14.6 | 3.0 | 3.7 | 1.5 |

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. An implant device for humans or mammals comprises:
a bone screw having an exposed surface;
one or more portions of the exposed surface having a bone formation enhancing 3-dimensional pattern; the 3-dimensional pattern forms a continuous network having voids having a void to solid ratio mimicking the void to faces or in the exposed shank surfaces or both, wherein the 3-dimensional pattern is a substantially continuous network having voids, wherein the voids have a width range of about 30-1000 microns wherein the 3-dimensional pattern mimics denticles of shark skin.

3. A bone screw for humans or mammals comprises:
a bone screw having exposed surfaces along a shank and threads extending from the shank;
one or more selected portions of the exposed surface having a 3-dimensional pattern, the pattern providing enhanced resistance to thread loosening when affixed to bone, wherein the exposed surface is on exterior portions of the threads or portions of the shank or both, wherein the one or more selected portions of the exposed portions having a bone formation enhancing 3-dimensional patterns are in the external exposed thread surfaces or in the exposed shank surfaces or both, wherein the 3-dimensional pattern is a substantially continuous network having voids, wherein the voids have a width range of about 30-1000 microns, wherein the bone formation 3-dimensional pattern has a void to solid ratio mimicking a pre-natal cancellous bone in a human and wherein the pattern mimics a marine or sea mammal bone structure and wherein the bone pattern exhibits the following characteristics

| BIOPSY | BV/TV | BS/BV | TbTh | TbSp | TbN | Ost # |
|---|---|---|---|---|---|---|
| Cross | 17.71 | 14.98 | 135.16 | 631.70 | 1.33 | 230/mm$^2$ |
| Long | 24.54 | 8.67 | 231.05 | 710.98 | 1.06 | 150/mm$^2$. |

4. A bone screw for humans or mammals comprises:
a bone screw having exposed surfaces along a shank and threads extending from the shank;
one or more selected portions of the exposed surface having a 3-dimensional pattern, the pattern providing enhanced resistance to thread loosening when affixed to bone, wherein the exposed surface is on exterior portions of the threads or portions of the shank or both, wherein the one or more selected portions of the exposed portions having a bone formation enhancing 3-dimensional patterns are in the external exposed thread surfaces or in the exposed shank surfaces or both, wherein the 3-dimensional pattern is a substantially continuous network having voids, wherein the voids have a width range of about 30-1000 microns wherein the 3-dimensional pattern has a facing along the threads that is directionally low in resistance during screw installation and tightening and once installed and tightened against bone has increased loosening resistance.

5. The bone screw for humans or mammals of claim 4 wherein at least 10 percent of said voids have a dimension of at least 30 microns.

6. The bone screw for humans or mammals of claim 4 wherein the voids have a depth into the selected surface of about 150 microns or less.

7. The bone screw for humans or mammals of claim 4 wherein the bone screw is made of a metal suitable for implanting in a human or mammal.

8. The bone screw for humans or mammals of claim 7 wherein the metal is titanium or a titanium alloy.

9. The bone screw for humans or mammals of claim 7 wherein the metal is stainless steel or a stainless steel alloy.

10. The bone screw for humans or mammals of claim 4 may include the 3-dimensional pattern to secure the screw to the skeletal bone structure with the pattern being on a proximal surface of the threads.

11. The bone screw for humans or mammals of claim 4 wherein the bone formation 3-dimensional pattern has a void to solid ratio mimicking a pre-natal cancellous bone in a human.

12. The bone screw for humans or mammals of claim 4 wherein the pattern mimics a marine or sea mammal bone structure.

13. The bone screw for humans or mammals of claim 12 wherein the sea or marine mammal is a whale.

14. The bone screw for humans or mammals of claim 12 wherein the sea or marine mammal is a dolphin.

15. The bone screw for humans or mammals of claim 12 wherein the implant at select portions exhibits a stress neutral isotropic structure for enhancing bone formation.

16. The bone screw for humans or mammals of claim 4 wherein the voids have a medium width of 500-800 microns in the open marrow regions of the bone screw when formed as a trabecular bone structure.

17. The bone screw for humans or mammals of claim 4 wherein the facing is asymmetrical in relation to torque resistance.

18. The bone screw for humans or mammals of claim 4 wherein the 3-dimensional pattern has a surface texture that forms a surface topography that is repeated on a regular, irregular, isotropic or asymmetrical, orthogonal or random basis.

19. The bone screw for humans or mammals of claim 4 wherein the 3-dimensional pattern is formed into a continuous network of troughs or channels.

20. The bone screw for humans or mammals of claim 4 wherein the 3-dimensional pattern is formed into a continuous network of ridges or protrusions.

21. The bone screw for humans or mammals of claim 4 wherein the 3-dimensional pattern is a combination of a continuous network of troughs or channels and ridges or protrusions.

* * * * *